(12) United States Patent
Dove

(10) Patent No.: US 6,579,940 B1
(45) Date of Patent: Jun. 17, 2003

(54) THERMOPLASTIC ELASTOMERIC MATERIAL AS A REPLACEMENT FOR NATURAL RUBBER LATEX

(75) Inventor: Jeffrey S. Dove, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/429,221

(22) Filed: Oct. 28, 1999

(51) Int. Cl.[7] .............................. C08L 9/06; C08L 53/02
(52) U.S. Cl. ..................... 525/98; 525/95; 525/280; 525/331.9; 525/332.2; 525/333.1; 525/333.4
(58) Field of Search .......................... 525/98, 95, 280, 525/331.9, 332.2, 333.1, 333.4

(56) References Cited

U.S. PATENT DOCUMENTS

| | | |
|---|---|---|
| 3,078,254 A | 2/1963 | Zelinski et al. |
| 3,135,716 A | 6/1964 | Uraneck et al. |
| 3,149,182 A | 9/1964 | Porter |
| 3,231,635 A | 1/1966 | Holden et al. |
| 3,265,765 A | 8/1966 | Holden et al. |
| 3,280,084 A | 10/1966 | Zellinski et al. |
| 3,281,383 A | 10/1966 | Zelinski et al. |
| 3,322,856 A | 5/1967 | Holden et al. |
| 3,390,207 A | 6/1968 | Moss et al. |
| 3,468,972 A | 9/1969 | Hsieh |
| 3,576,912 A | 4/1971 | Winkler |
| 3,594,452 A | 7/1971 | De La Mare et al. |
| 3,595,941 A | 7/1971 | Farrar et al. |
| 3,598,887 A | 8/1971 | Darcy et al. |
| 3,624,057 A | 11/1971 | Farrar |
| 3,632,682 A | 1/1972 | Darcy |
| 3,639,521 A | 2/1972 | Hsieh |
| 3,652,516 A | 3/1972 | Farrar |
| 3,700,633 A | 10/1972 | Wald et al. |
| 3,734,973 A | 5/1973 | Farrar |
| 3,766,301 A | 10/1973 | De La Mare et al. |
| 3,778,490 A | 12/1973 | Hsieh |
| 3,784,637 A | 1/1974 | Farrar |
| 3,949,020 A | 4/1976 | Prudence |
| 3,985,830 A | 10/1976 | Fetters et al. |
| 4,010,226 A | 3/1977 | Crossland et al. |
| 4,086,406 A | 4/1978 | Trepka |
| 4,248,981 A | 2/1981 | Milkovich et al. |
| 4,391,949 A | 7/1983 | St. Clair |
| 4,556,464 A | * 12/1985 | St. Clair |
| 4,572,819 A | 2/1986 | Priddy et al. |
| 4,600,749 A | 7/1986 | Minekawa et al. |
| 4,725,654 A | 2/1988 | Priddy et al. |
| 5,055,519 A | 10/1991 | Ono et al. |
| 5,223,568 A | 6/1993 | Landi et al. |
| 5,264,488 A | 11/1993 | Takeuchi et al. |
| 5,276,100 A | 1/1994 | Coolbaugh et al. |
| 5,292,820 A | 3/1994 | Coolbaugh et al. |
| 5,360,875 A | 11/1994 | Masse et al. |
| 5,385,994 A | 1/1995 | Graves et al. |
| 5,407,715 A | 4/1995 | Buddenhagen et al. |
| 5,412,032 A | * 5/1995 | Hansen et al. ............... 525/98 |
| 5,438,102 A | 8/1995 | Brandes et al. |
| 5,464,914 A | 11/1995 | Lo et al. |
| 5,556,383 A | 9/1996 | Wang et al. |
| 5,663,239 A | 9/1997 | Coolbaugh et al. |
| 5,786,426 A | 7/1998 | Sperling et al. |
| 5,830,182 A | 11/1998 | Wang et al. |
| 5,849,846 A | 12/1998 | Chen et al. |
| 5,951,941 A | 9/1999 | Wang et al. |
| 5,997,969 A | 12/1999 | Gardon |

FOREIGN PATENT DOCUMENTS

| | | |
|---|---|---|
| CA | 762544 | 7/1967 |
| EP | 0 214 721 | 3/1987 |
| EP | 0 335 664 | 10/1989 |
| EP | 0379951 | 1/1990 |
| EP | 0472749 | 4/1992 |
| EP | 0 488 021 A1 | 6/1992 |
| EP | 0254346 | 1/1993 |
| EP | 0 523 928 A2 | 1/1993 |
| EP | 0682041 | 11/1995 |
| EP | 0690075 | 1/1996 |
| EP | 0723981 | 7/1996 |
| GB | 1025295 | 4/1966 |
| GB | 1035873 | 7/1966 |
| GB | 1187358 | 4/1970 |
| GB | 1 278 259 | 1/1972 |
| GB | 1 460 445 | 1/1977 |
| GB | 1 512 557 | 6/1978 |
| GB | 2 008 140 A | 5/1979 |
| NL | 6401809 | 8/1964 |
| WO | WO 94/20574 | 9/1994 |
| WO | WO 98/39044 | 9/1998 |
| WO | WO 99/13924 | 3/1999 |

* cited by examiner

Primary Examiner—James J. Seidleck
Assistant Examiner—Olga Asinovsky
(74) Attorney, Agent, or Firm—Louis Cullman; Lena Vinitskaya

(57) ABSTRACT

The present invention provides functionally modified thermoplastic elastomeric compounds composed of at least one polystyrene hard domain, at least one polyolefin rubber domain and at least one cross-linkable compound interspersed within one or more of the domains. Methods for making and using these thermoplastic elastomeric compounds are also provided as are articles made from these compounds along with methods for making such articles.

27 Claims, No Drawings

THERMOPLASTIC ELASTOMERIC MATERIAL AS A REPLACEMENT FOR NATURAL RUBBER LATEX

FIELD OF INVENTION

This invention, generally is directed to thermoplastic elastomers, methods for their manufacture and use, and to physically and mechanically improved articles manufactured therefrom. More specifically the present invention provides new thermoplastic elastomeric compositions, articles and methods of making same which embody the desirable physical qualities normally associated with natural rubber latex in addition to markedly reduced allergenicity and significantly improved chemical and physical properties including solvent resistance, elasticity and resilience.

BACKGROUND OF THE INVENTION

Broadly stated, the present invention provides new enhanced thermoplastic elastomers having unique combinations of physical, chemical, and mechanical properties which make them particularly well suited for replacing natural rubber latex in articles traditionally made from natural rubber latex. More specifically, the present invention is directed to functionally enhanced thermoplastic elastomers incorporating unique cross-linkages such that the compositions function as elastomeric materials having aspects of thermoset material stability and function. These unique materials have been optimized to function as improved replacements for cured natural rubber latex while maintaining, and even surpassing the beneficial physical, chemical, and mechanical properties of natural rubber latex. Moreover, in addition to being readily applicable to the majority of existing latex article manufacturing processes, the thermoplastic elastomeric materials of the present invention possess the added benefit of being compatible with continuous manufacturing techniques including extrusion, blow forming, injection molding, rolling and sheet formation.

Articles manufactured from natural rubber latex exhibit a variety of desirable properties including resistance to creep (resisting the undesirable elongation of a material under constant stress), compression resistance (the ability of an article to return to its original size and volume after squeezing), elasticity, solvent and plasticizer resistance, and overall biocompatibility. Unfortunately, a primary drawback associated with natural rubber latex articles is the growing number of people that are allergic to them.

Early attempts at producing articles made from alternative non-natural rubber latex materials have been generally successful though not without their associated problems. Substitute artificial or synthetic latex materials are relatively expensive when compared to natural rubber latex and in some cases are considerably more expensive. More importantly, in most applications their physical, mechanical, and chemical properties are markedly inferior to those of natural rubber latex. For example, some artificial rubbers lack sufficient elasticity or strength to function effectively as gloves. Some are affected by solvents making them difficult to use around alcohols or naturally occurring oils which can soften and degrade the material. Others exhibit deforming material creep when subjected to constant stress. This can result in sagging and bagginess which make such materials inappropriate for inflation balloons or similar structures. Other latex replacements possess poor compression resistance and permanently deform when subjected to compressive stress. These inferior properties can make it difficult to package, store, or use articles manufactured from these alternative materials without damage.

Accordingly, it is a primary objective of the present invention to provide an effective material suitable for use as a replacement for natural rubber latex in the production of commercial and medical products. Concomitant with this objective is providing elastomeric replacement materials for natural rubber latex that can be incorporated into most existing continuous manufacturing processes without significant modification or expense.

It is an additional objective of the present invention to provide alternative materials, especially for medical devices and products, enhancing their physical, chemical, and mechanical properties and thus the functionality of these devices and products.

SUMMARY OF THE INVENTION

These and other objects are achieved by the present invention which provides novel biocompatible, nonallergenic thermoplastic elastomeric compounds, methods for producing these compounds and articles made therefrom. The novel compounds made in accordance with the teachings of the present invention provide functionally enhanced thermoplastic elastomers that, as compared to natural rubber latex, are less allergenic, possess increased elastomeric resilience, decreased creep, and increased resistance to oils, lipids and organic solvents while simultaneously eliminating many of the adverse properties which can significantly limit the natural product's utility.

Articles made from the thermoplastic elastomeric (TPE) compounds of the present invention possess excellent elasticity, exceptional resilience, exhibit minimal creep and resist swelling when exposed to oils, lipids and organic solvents, yet remain non-toxic. This unique combination of physical and biological properties results in a material that is ideally suited for medical devices and other products including those which may contain natural rubber latex.

In one embodiment of the present invention, the thermoplastic elastomeric compounds are composed of at least one thermoplastic elastomer comprising individual triblock sub-units containing two polystyrene hard domains and one polyolefin rubber domain. In accordance with the teachings of the present invention the individual triblocks are uniquely cross-linked using double bonds present in the polystyrene hard domain, the polyolefin rubber domain, or both in order to modify the properties of the material.

In another embodiment of the present invention, the TPE is composed of individual diblock sub-units containing one polystyrene hard domain and one polyolefin rubber domain. The individual diblocks may be linked together through their polyolefin rubber domains using suitable coupling agents forming dendritic structures. Further, the diblocks of the present invention can be used with, or without, coupling reagents to modify their properties.

When produced in accordance with the teachings of the present invention these compounds can be modified to contain additional unsaturated groups that can be further cross-linked to increase TPE entanglement. The extent of entanglement present in the TPE is a function of the number, type and location of the double bonds and contributes to the TPE's final character and functionality. This, in turn, is controlled by the raw materials used and reaction conditions selected utilizing the teachings of the present invention. Thus, utilizing the teachings of the present invention, the thermoplastic elastomeric compounds of the present invention can be modified or designed to exhibit a wide range of physical properties. Depending on the extent of cross-linking present in the materials, these compounds can possess physical properties ranging from thermoplastics to thermoset resins. Consequently, precise control of the properties and functions of the materials and articles of the present invention can be achieved. This provides yet another advantageous aspect of the present invention and significantly increases the options available to materials engineers, product designers, and end users.

An initial step in the exemplary methods of producing thermoplastic elastomeric compounds of the present invention involves providing styrene monomers with a lithium catalyst in the presence of suitable olefin monomers such as isoprene or 1,3-butadiene. Additional alkyl and aryl compounds containing vinyl-type groups, coupling reagents, and/or halogen containing compounds may be added to the reaction mixtures resulting in a number of different TPE material classes including base TPEs, high strength TPEs and entanglement TPEs, each exhibiting its own combination of superior physical and chemical properties relative to natural rubber latex.

In the next step of the exemplary methods of the present invention, a final elastomer is completed using at least one base TPE from the preceding step, which may be mixed with one or more high strength TPEs or entanglement TPEs, plus antioxidants/antiozonates, mineral oil, silanated silica and/or chemical cross-linking agents such as sulfur (also known as vulcanization agents or "packages") to produce a TPE with the desired physical properties. The thermoplastic elastomers of the present invention so produced can then be used to manufacture articles such as balloon catheters or surgical gloves which can then be cured and cross-linked using methods such as, but not limited to, electron beam radiation, gamma radiation, or chemical vulcanization.

Further objects and advantages of the methods, compositions and articles of manufacture produced in accordance with the teachings of the present invention, as well as a better understanding thereof, will be afforded to those skilled in the art from a consideration of the following detailed explanation of exemplary embodiments thereof.

DETAILED DESCRIPTION OF EXEMPLARY EMBODIMENTS

In a broad aspect, the thermoplastic elastomeric compounds of the present invention are formed from copolymers of at least one polystyrene hard domain and at least one polyolefin rubber domain that are controllably cross-linked to produce a wide range of desirable physical, chemical, and biological properties. Each of these copolymers may be composed of a single polyolefin rubber domain with either one or two polystyrene hard domain end caps. Additionally, in accordance with the teachings of the present invention, further improvements in functional performance can be produced by incorporating unsaturated aryl and/or alkyl compounds as disclosed herein, which will controllably increase cross-linking and interchain entanglement, within the thermoplastic elastomers (TPE). In accordance with the teachings of the present invention these unsaturated compounds can be incorporated into one or more polystyrene or polyolefin domains.

Generally speaking, compounds of the present invention can be considered TPEs. Moreover, these TPEs can be designed to be cross-linked extensively in order to exhibit near thermoset properties. Alternatively, utilizing the teachings of the present invention enables these TPEs to be configures with less cross-linking in order to function more like thermoplastics. Thus, different compound formulations made in accordance with the teachings of the present invention can produce TPEs designed to accentuate or enhance specific physical or functional properties. These designed compounds can be grouped according to their intended properties or applications. By way of example only, and not intended to limit the present invention to these groupings alone, the various TPEs of the preset invention can be categorized broadly as Base TPEs, High Strength TPEs and Entanglement TPEs.

These highly versatile compounds of the present invention can be designed to possess beneficial properties for use in specific articles designed for specific applications. As disclosed, this can be accomplished by mixing or adding other property modifying compounds such as mineral oils, silica, antioxidants/antiozonates and vulcanization materials with individual TPEs or combinations thereof. These combinations of TPEs and/or these property modifiers can then be formed into articles of manufacture which are either chemically or physically cross-linked as desired utilizing the teachings of the present invention. The resulting articles exhibit chosen or desired physical properties specifically engineered for particular applications that are different from those of natural rubber latex. Plus, they are nearly immunologically inert and therefore exibit nonallergenic qualities.

More specifically, the present invention provides functionally enhanced thermoplastic elastomeric copolymers which are optimized to function as improved replacements for cured natural rubber latex and which are highly resistant to solvation or plasticizing by aliphatic or aromatic solvents and oils. The polystyrene/polyolefin thermoplastic elastomeric copolymers may also substantially eliminate alleged allergen problems associated with natural latex rubber and will maintain or optimize known beneficial properties such as ultraviolet and ozone resistance, elasticity, fatigue resistance, resistance to creep, tensile strength and biocompatibility. Thus, as will be appreciated by those skilled in the art, the thermoplastic elastomeric materials of the present invention are particularly well suited for use in the production of commercial and medical products.

In contrast to the present invention, traditional polystyrene/polyolefin elastomeric materials having polystyrene domains together with polyolefin rubber domains are known in the art. These elastomeric copolymers may be synthesized by first polymerizing styrene monomers with a lithium salt catalyst, preferably butyl lithium, such that a "living polymer" is created. A "living polymer" is defined as a styrene polymer, (A), wherein the lithium catalyst is not consumed by the reaction but remains bound to the beta carbon of the terminal vinyl group; thereby remaining available to react with newly added monomers.

The polyolefin rubber domain, (B), of these known materials are typically polymerized with (A) the styrene domain, such that an (AB)n diblock copolymer is formed. Typically, the polyolefin rubber domains (B) are made from either 1,3 butadiene or isoprene due to the high degree of solubility in manufacturing solvents exhibited by these compounds. The final step in the traditional ABA triblock polymer formation is the addition of new styrene monomer and lithium catalyst such that a second polystyrene end cap is formed polymerized with the rubber domain of the existing (AB)n polymer, hence an ABA triblock is formed.

These known ABA triblock polymers discussed above are commonly known as either SBS or SIS polymers depending upon whether butadiene (B) or isoprene (I) is copolymerized with styrene (S). These are available commercially from companies such as Shell Oil which markets their ABA triblock polymer under the trade name Kraton®.

While these prior art ABA triblock polymers have been used with limited success as rubber substitutes, relative to natural rubber latex, their susceptibility to shear stress, solvents and creep in addition to other inferior properties have made them undesirable as latex substitutes, particularly in personal or medical applications. One embodiment of the present invention addresses some of these and other drawbacks by producing articles made from SIS and SBS triblock polymers; however, in accordance with the teachings of the present invention, unsaturated groups in the polyolefin domains of these materials are uniquely cross-linked following formation and manufacturing of the articles as part of the curing step. Cross-linking processes for practicing the present invention include, but are not limited to, electron beam radiation (E-beam), gamma radiation and chemical vulcanization processes. These novel post formation cross-linking processes practiced in accordance with the teachings of the present invention improve resistance to creep and reduce elastic memory. Thus, articles manufactured in accordance with the teachings of the present invention are markedly superior. However, it will be appreciated that these cross-linked TPEs may still exhibit swelling on contact with organic solvents and lipids limiting their utility to specific, solvent free applications.

In an alternative embodiment of the present invention, a precursor to the previously disclosed ABA triblock copolymer, known as an (AB)n diblock polymer, is synthesized by adding either isoprene or butadiene to a reaction mixture containing butyl lithium and styrene. The resultant (AB)n diblock copolymer so produced has a polystyrene hard domain attached to a polyolefin rubber domain which, unlike the ABA polymer, are not coupled to a second polystyrene hard domain or end cap. In accordance with the teachings of the present invention, during the polymerization process, coupling agents, such as hexachlorodisilane, trichlorosilane or silicon tetrachloride are added to the reaction mixture. These coupling agents complex with the free ends of the (AB)n rubber domains to form star-shaped, or dendretic, polymers.

These resulting dendretic polymers are then formed or extruded into manufactured articles and cross-linked during the curing phase as with the previously discussed embodiment of the present invention. The final manufactured articles have much higher degrees of rubber domain cross-linking which, in accordance with the teachings of the resent invention, increase the creep resistance and reduce the elastic memory of the polymers and articles. However, the cross-linking is limited to double bonds in the rubber domain; these (AB)n polymers may lack organic solvent and lipid resistance. Therefore, while these methods and polymers are contemplated as being within the scope of the present invention, and are clearly superior to the prior art, there are circumstances requiring a need for organic solvent and lipid resistance. The present invention also addresses these needs.

In the exemplary alternative embodiments of the present invention which follow, polymer swelling as a result of exposure to organic solvents and lipids is overcome by significantly increasing the number of unsaturated groups in the polyolefin rubber domains or in the polystyrene hard domains, or both, during polymerization. The resulting compounds are cross-linked in accordance with the teachings of the present invention which produces complex cross-linked polymer structures which exhibit increased resistance to creep, reduced elastic memory, and substantially superior resistance to organic solvents and lipids.

In one exemplary embodiment of the present invention, alkyl/aryl cross-linkable compounds are added to the inventive reaction mixture containing styrene monomers and a butyl lithium catalyst. Exemplary alkyl/aryl cross-linkable compounds in accordance with the teachings of the present invention include, but are not limited to, vinylcyclohexane, 1-phenyl-1,3-butadiene, 1,4-diphenyl-1,3-butadiene, 1,2-dimethylene cyclohexane, 1,2-dimethylene cyclopentane, cyclopetadiene, 1,3-butadiene, and isoprene. Similarly, exemplary branching alkyl/aryl cross-linkable compounds include, but are not limited to, divinyl benzene, 6,6 dimethyl fulvene, and myracene.

Once these, or equivalent cross-linkable compounds have been incorporated into the polystyrene hard domains as disclosed, (AB)n diblock or ABA triblock polymers can be formed and used in accordance with the teachings of the present invention as described above. Unlike the prior art, the resultant new TPE compositions so produced, now possess reactive unsaturated groups interspersed throughout their styrene hard domain end caps. In accordance with the teachings of the present invention, these reactive unsaturated groups will form additional cross-links between adjacent styrene and/or rubber domains following post formation or manufacturing curing. These additional cross-linkers can be configured to modify the physical, chemical, and mechanical properties of these materials and articles so produced, without increasing allergenicity.

In an alternative embodiment of the present invention the polystyrene hard domains can be further modified to contain additional cross-linkable moieties by adding para or meta derivatives of styrene to the catalyzed styrene reaction mixture. Non-limiting examples of these styrene derivatives include acetate and propionate esters, xanthates, borates, sulfites, tosyls, carbonates, carbamates, and thiocarbamates. Such styrene derivatives are highly stable and non-reactive (do not undergo spontaneous cross-linking) during the polymerization process. However, the heat associated with normal extrusion processes, or other thermoplastic formation or manufacturing processes, is sufficient to generate additional pendent vinyl type groups. Thus, following extrusion or manufacture, these newly formed vinyl groups can be cross-linked during the curing stage using any one of the aforementioned methods of this invention. The resulting articles possess enhanced resistance to creep, to solvation as well as reduced elastic memory. In an analogous fashion, within the teachings of the present invention, additional disulfide and polysulfide (sulfan) cross-linking functionality can be added to the polystyrene hard domains by adding styrene monomers substituted at the meta or para position with sulfhydral groups to the catalyzed styrene mixture. This further adds to the ability of the present invention to produce TPEs having specific properties and ranges of properties.

In yet another alternative embodiment of the present invention, further resistance to solvation can be imparted to the present invention by adding halogen functionality to the polystyrene hard domains. In an exemplary process, halogen derivatives of styrene such as, but not limited to, 4-chlorostyrene are added to the catalyzed styrene reaction mixture. Alternatively, halogen functionalities to the styrene hard domains can be accomplished after the polymerization is complete by partially halogenating existing double bonds within the polymer. This process can be analogous to those known in the chemical arts for producing vicinal dihalides or hydrogen halides. Post-polymerization halogenation of unsaturated residues within the thermoplastic elastomer significantly reduces the polymers' susceptibility to ozone and to ultraviolet light degradation, in addition to increasing their solvent resistance.

The polyolefin rubber domains of the thermoplastic elastomers of the present invention can also be modified to enrich their level of unsaturation if desired within the teachings of the present invention. The resultant increased amount of cross-linkable reactive sites within the rubber domain adds significantly to the amount of intra-molecular cross-linking and entanglement between the polyolefin rubber domains and/or the polystyrene hard domain end caps when such modified starting materials are cured. This also adds to the ability of the present invention to fine tune the physical, chemical, and mechanical properties of this novel thermoplastic elastomer in order to meet or exceed the properties of natural rubber latex.

More specifically, branched alkyl and aryl cross-linkable compounds including, but not limited to, divinyl benzene, 6,6-dimethyl fulvene and myracene can be added during the butadiene or isoprene polymerization steps of the present invention. Butadiene and isoprene derivatives which generate pendent vinyl groups from the heat of normal extrusion or the manufacturing processes such as rolling, blow molding, etc. can also be added during the polyolefin rubber domain polymerization. This can be accomplished with methods similar to the methods described in connection with the polystyrene hard domain end caps. The aforementioned butadiene and isoprene derivatives include, but are not limited to esters, xanthates, borate, sulfites, tosyls, carbonates, carbamates and thiocarbamates. Disulfide and polysulfide functionality can also be added to the polyolefin rubber domains in an analogous fashion in accordance with the teachings of the present invention.

Similarly, halogen functionality can be added to the polyolefin rubber domains during the polymerization process using halo-derivatives of butadiene and/or isoprene such as chloroisoprene or by post polymerization halogenation as described above.

Additional materials may be added to enhance specific material performance criteria utilizing the teachings of the present invention. These additional materials may include antioxidants, antiozonates, reinforcing fillers, and particular cross-linkable compounds, depending upon the properties desired.

It is important to note that none of the various processes and modifications of the present invention are mutually exclusive. Any combination of cross-linkable compounds, cross-linking agents or post-processing treatments may be used within the scope and teachings of the present invention. The exact extent of cross-linking and/or unsaturation can be adjusted utilizing these teachings to produce a thermoplastic elastomer article possessing a wide range of combinations of expandability, elastic memory, solvent and lipid resistance and resistance to creep.

A more specific exemplary cross-linking step of the present invention includes incorporating a quantity of cross-linkable monomer within a range of about 1% to 20% by weight with one of the polystyrene/polyolefin reactants prior to the curing phase. For example, the cross-linkable monomer may be incorporated with the styrene reactant after all of a catalyst such as butyl lithium and an initiator have been incorporated into the material during the polymerization reaction. An exemplary styrenic cross-linkable compound appropriate to the method of the present invention is isoprene.

Alternatively, an additional cross-linking step may include incorporating a vinyl coupler between adjacent styrene units in the material. For example, 1,4-diphenyl, 1,3-butadiene, acetylene or propyne may be substituted in place of isoprene. With these exemplary vinyl couplers, a higher glass transition temperature can be maintained and lower miscibility of the polyolefin rubber domain of the polystyrene hard domains can be achieved.

If desired, a compatibilizer polymer may be used to aid in dispersion or solubilization of dissimilar polymers into a new uniform material, thereby blending the properties of the dissimilar polymers in accordance with the teachings of the present invention. For example, it is contemplated that an exemplary compatibilizer, such as polychlorloprene (also known as Neoprene), can be added to the reaction mixture in order to improve the thermoplastic elastomeric polymer's resistance to oils and plasticizers. Polychlorloprene can either be augmented with, or replaced by, such compounds as halobutyl rubber, and/or hydrogenated butyl elastomer rubber modifiers. These compatibilizer polymers also enhance polymer chain entanglements, particularly after any cross-linking occurs. The resultant polymer chain entanglements improve elasticity and resilience of the TPEs. Alternate materials which may be added to the TPEs of the present invention are linear or cyclic polybutadiene "compatibilizer" polymers that exhibit a low, broad molecular weight distribution. One such compatibilizer polymer is manufactured by Huls Aktiengesell-Schaft and is known as Vestenamer®, manufactured in Marl, Germany.

Without wishing to be limited, a particularly illustrative example of the unique physical, chemical, and mechanical properties of the thermoplastic elastomeric materials of the present invention is illustrated by the use of such materials as substitutes for natural rubber latex in the manufacture of thermodilution type Swan-Ganz monitoring balloon catheters. This type of balloon catheter has a geometry which requires the balloon to have at least a 1,200% working extension ratio. Additionally, the balloon material must withstand sterilization, and have an 18-month shelf life. The balloon must also survive direct blood contact for at least three days within a patient during which the balloon is repeatedly inflated approximately 100 times. Under these conditions, within a living being, the balloon must not rupture, distort, creep or become eccentric, and must survive routine insertion, maneuvering and withdrawal procedures. Balloon materials must also be non-thrombogenic, non-toxic and otherwise biocompatible for direct intravascular patient contact for a minimum of 72 hours.

The thermoplastic elastomeric materials of the present invention address these difficulties by providing unique polymer combinations with enhanced physical and chemical properties required for the Swan-Ganz monitoring balloon catheter and for other in vivo devices. Similarly, the thermoplastic elastomeric materials and associated methods for making and using the materials of the present invention are also useful in producing improved products such as urethral catheters, cardiovascular catheters, gloves, bandages, tapes, blood pressure cuffs, condoms or coverings and instrument components. The physical, chemical, and mechanical properties of these products can be fine tuned and optimized for the intended working environment.

Presented below are examples of particular exemplary thermoplastic elastomers based on the methods and teachings of the present invention. These examples are presented to describe specific embodiments of the present invention but are not intended to limit the scope of what is claimed.

EXAMPLES

Thermoplastic elastomers (TPE) can be formulated to possess various physical properties. In Table 1 base elastomers are formulated for use with either chemical or radiation cross-linking in accordance with the teachings of the present invention. Table 2 gives the basic formula for producing a high strength radiation cross-linked reinforcing TPE polymer. Similarly, utilizing the teachings of the present invention, entanglement TPEs can be formulated which improve resultant materials' resilience (Table 3) and can also be used with either chemical or radiation cross-linkers.

elastomers possessing physical, mechanical, and chemical properties appropriate for specific applications. Table 4 lists five such non-limiting examples which may, or may not, be

TABLE 1

Base Thermoplastic Elastomer (TPE) According to the Present Invention

| TPE Type | Molecular weight of styrene domain | Percent unsaturation of styrene domain | Multi-functional styrene domain monomer | Molecular weight of rubber arm | Monomer type in rubber domain | Percent chlorine | Number of arms | Coupler type | Preferred cross-linking method |
|---|---|---|---|---|---|---|---|---|---|
| II | 7.5 k | 5 | Phenyl Butadiene | 40 k | Butadiene | 3 | 2 | dichlorosilane | radiation |
| IV | 7.5 k | 5 | Isoprene | 40 k | Isoprene | 3 | 4 | silicon tetrachloride | chemical |

TABLE 2

High Strength TPE

| TPE Type | Molecular weight of styrene domain | Percent unsaturation of styrene domain | Multi-functional styrene domain monomer | Molecular weight of rubber arm | Monomer Type in Rubber Domain | Percent chlorine | Number of arms | Coupler type | Preferred cross-linking method |
|---|---|---|---|---|---|---|---|---|---|
| V | 15 k | 10 | Diphenyl butadiene | 150 k | 1,2 di-methylene cyclohexane | 0 | 2 | dichlorosilane | radiation |

TABLE 3

Entangled TPE

| TPE Type | Molecular weight of styrene domain | Percent unsaturation of styrene domain | Multi-functional styrene domain monomer | Molecular weight of rubber arm | Monomer Type in Rubber Domain | Percent chlorine | Number of arms | Coupler type | Preferred cross-linking method |
|---|---|---|---|---|---|---|---|---|---|
| I | 5 k | 5 | Butadiene | 15 k | Butadiene | 0 | 6 | hexachloro disilane | radiation |
| III | 5 k | 0 | NA | 15 k | Isoprene | 3 | 6 | hexachloro disilane | chemical |

The thermoplastic elastomers produced in accordance with the present invention can be combined to produce combined with silicated silicas and antioxidants/antiozonates.

TABLE 4

Examples of Novel TPEs

| Novel TPE | Base TPE and Percent | High Strength TPE and Percent | Entangled TPE and Percent | Mineral Oil | Silanted Silica | Percent Antioxidant/Antiozonate | Percent Vulcanization Package |
|---|---|---|---|---|---|---|---|
| 1 | II/75 | 0 | I/10 | NA | NA | 3 | 0 |
| 2 | II/68 | V/2 | I/10 | 15 | 2 | 3 | 0 |
| 3 | II/82 | V/5 | I/5 | 0 | 5 | 3 | 0 |
| 4 | IV/75 | 0 | III/10 | 0 | 2 | 3 | 10 |
| 5 | IV/62 | V/5 | III/15 | 0 | 0 | 3 | 15 |

1. Radiation Cross-linked Medium Modulus Rubber
2. Radiation Cross-linked Low Modulus Rubber
3. Radiation Cross-linked High Modulus Rubber
4. Sulfur Cross-linked Medium Modulus Rubber
5. Sulfur Cross-linked High Modulus Rubber Examples of suitable silanated silica compounds useful in the practice of the present invention include, but are not limited to, silane coupled vinyl, styryl, thiol, and sulfan functional groups on fumed silica fillers such as Cab-o-sil® M-5. These compounds act as reinforcing fillers which improve fatigue resistance and tensile strength in the finished products of the present invention. Preferred fillers possess a high surface area fumed with silica, particularly with a silane type surface treatment. This treatment would result in covalently bound polysulfide, sulfan and/or alkyl diene groups. This type of filler treatment improves compatibility and amplifies filler enhancement effects. These surface treated fillers directly cross-link to the polymer backbone. The polysulfan filler has the property of providing a long-lasting polysulfidic linkage over the life of the final material. Cab-o-sil® is manufactured by Cabot Corporation, Boston, Mass.

Non-limiting examples of appropriate antioxidants/antiozonates include phenolics, thioesters, polyalkylamines, polyarylamines and parafinic waxes. As discussed above, the type of cross-linking carried out utilizing the teachings of the present invention can significantly influence the final characteristics of the thermoplastic material. In Table 4, non-limiting examples of radiation cross-linked and vulcanized (sulfur cross-linked) materials are shown. Suitable vulcanization packages may contain, but are not limited to, sulfur, zinc oxide, steric acid, accelerators, and anti-scorch agents. Additional combinations for vulcanization packages are known in the art. Other materials may be added to the cross-linked elastomer in order to modify color, opacity and other physical features as desired.

Once the final composition for a particular thermoplastic elastomer made in accordance with the present invention has been determined, an article can be formed using manufacturing techniques known in the art such as blow forming, injection molding, rolling and sheet formation and, preferably, extrusion techniques.

Similarly, the final step in manufacturing the materials and articles of the present invention is cross-linking the thermoplastic elastomers utilizing a variety of techniques. For example, E-beam radiation is one useful mechanism for improving cross-linking. One potential disadvantage of E-beam radiation is that polymer chain bonds are broken as well as cross-linked during this process. In the worst case, at high doses of radiation, the polymer will degrade and become unstable.

Alternatively, chemical cross-linking with materials such as peroxides, vulcanizing with sulfur, and treatment with bis-Malamids introduces cross-links without breaking the backbone of the polymer.

The enhanced property thermoplastic elastomeric latex replacement materials of the present invention are particularly well suited to function as substitutes for natural rubber latex. As an added benefit, these latex replacement materials also maintain, and even optimize known beneficial properties such as ultraviolet and ozone resistance, fatigue resistance, tensile strength, solvent resistance, as well as plasticizer resistance. Furthermore, these thermoplastic elastomeric materials are biocompatible, inhibit blood clotting and are not susceptible to dissolution in vivo.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. A method for making a thermoplastic elastomeric article comprising:

forming a mixture having a polystyrene hard domain, a polyolefin rubber domain and a coupling agent, wherein at least one alkyl cross-linkable compound and/or at least one aryl cross-linkable compound is interspersed within said polystyrene hard domain and wherein said aryl cross-linkable compound is different from the monomer used to form said polystyrene hard domain;

polymerizing said mixture to form a copolymer having the general formula $(AB)_n$ wherein A is said polystyrene hard domain, B is said polyolefin rubber domain;

forming a solid article from said copolymer; and cross-linking said cross-linkable compound in said copolymer.

2. The method for making a thermoplastic elastomeric article according to claim 1 further comprising:

interspersing within said polyolefin rubber domain at least one alkyl cross-linkable compound and/or at least one aryl cross-linkable compound prior to polymerizing said mixture wherein said alkyl cross-linkable compound is different from the monomer used to form said polyolefin rubber domain.

3. The method according to claim 1 wherein said solid article is selected from the group consisting of catheters, gloves, bandages, tapes, blood pressure cuffs and condoms.

4. The method according to claim 1 wherein said at least one cross-linkable compound is selected from the group consisting of 1,2-dimethylene cyclohexane, 1,2-dimethylene cyclopentane, cyclopentadiene, 1,3-butadiene, isoprene, vinylcyclohexane, 6,6-dimethylfulvene, myracene, 1-phenyl-1,3-butadiene, 1,4-diphenyl-1,3-butadiene, divinyl benzene, and combinations thereof.

5. The method according to claim 1 wherein said cross-linking step is accomplished using a process selected from the group consisting of electron beam radiation, gamma radiation, and chemical vulcanization.

6. The method according to claim 1 wherein said step of forming said solid article is selected from the group consisting of rolling, blow molding, blow forming, injection molding and extrusion.

7. A thermoplastic elastomer (TPE) comprising:

a copolymer having the general formula (AB)n wherein A is a polystyrene hard domain, B is a polyolefin rubber domain and n is an integer, wherein at least one alkyl cross-linkable compound and/or at least one aryl cross-linkable compound is interspersed within said polystyrene hard domain, wherein said aryl cross-linkable compound is different from the monomer used to form said polystyrene hard domain, and wherein said (AB)n copolymer has free ends, said free ends being coupled using at least one coupling agent.

8. The thermoplastic elastomer (TPE) according to claim 7 further comprising at least one additional alkyl cross-linkable compound and/or at least one aryl cross-linkable compound interspersed within said polyolefin rubber domain wherein said additional alkyl cross-linkable compound is different from the monomer used to form the polyolefin rubber domain.

9. The thermoplastic elastomer (TPE) according to claim 7, wherein said cross-linkable compound is a cross-linkable monomer within a range of about 1% to 20% by weight of, and mixed with, one of the polystyrene hard domain or polyolefin rubber domain components.

10. The thermoplastic elastomer (TPE) according to claim 7, wherein said polyolefin rubber domain is selected from the group consisting of isoprene and 1,3-butadiene.

11. The thermoplastic elastomer (TPE) according to claim 7, wherein said at least one cross-linkable compound is selected from the group consisting of 1,2-dimethylene cyclohexane, 1,2-dimethylene cyclopentane, cyclopentadiene, 1,3 butadiene, isoprene, vinylcyclohexane, 6,6-dimethylfulvene, myracene, 1-phenyl-1,3-butadiene, 1,4-diphenyl-1,3-butadiene, divinyl benzene, and combinations thereof.

12. The thermoplastic elastomer (TPE) according to claim 7, further comprising at least one antioxidant.

13. The thermoplastic elastomer (TPE) according to claim 7, wherein said at least one antioxidant is selected from the group consisting of phenolics, thioesters, polyalkylamines, polyarylamines and paraffinic waxes.

14. The thermoplastic elastomer (TPE) according to claim 7, further comprising a silanated silica.

15. The thermoplastic elastomer (TPE) according to claim 14, wherein said silanated silica is a silane coupled fumed silica filler.

16. The thermoplastic elastomer (TPE) according to claim 7, further comprising mineral oil.

17. The thermoplastic elastomer (TPE) according to claim 7, further comprising a vulcanization package.

18. The thermoplastic elastomer (TPE) according to claim 17 wherein said vulcanization package is selected from the group consisting of sulfur, zinc oxide, steric acid, accelerators and anti-scorch agents.

19. The thermoplastic elastomer (TPE) according to claim 7, wherein said coupling reagent is trichlorosilane or silicon tetrachloride.

20. The thermoplastic elastomer (TPE) according to claim 7, wherein said polystyrene hard domain (A) is cross-linked using a process selected from the group consisting of electron beam radiation, gamma radiation or chemical vulcanization.

21. A balloon catheter comprised of the thermoplastic elastomer of claim 7.

22. A urethral catheter comprised of the thermoplastic elastomer of claim 7.

23. A glove comprised of the thermoplastic elastomer of claim 7.

24. A bandage comprised of the thermoplastic elastomer of claim 7.

25. A tape comprised of the thermoplastic elastomer of claim 7.

26. A blood pressure cuff comprised of the thermoplastic elastomer of claim 7.

27. A condom comprised of the thermoplastic elastomer of claim 7.

* * * * *